United States Patent
Pacetti et al.

(10) Patent No.: US 9,539,332 B2
(45) Date of Patent: Jan. 10, 2017

(54) PLASTICIZERS FOR COATING COMPOSITIONS

(71) Applicant: Abbott Cardiovascular Systems Inc., Santa Clara, CA (US)

(72) Inventors: Stephen Dirk Pacetti, San Jose, CA (US); Yiwen Tang, Sunnyvale, CA (US); Syed Faiyaz Ahmed Hossainy, Hayward, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/621,301

(22) Filed: Feb. 12, 2015

(65) Prior Publication Data

US 2015/0150989 A1  Jun. 4, 2015

Related U.S. Application Data

(63) Continuation of application No. 12/475,296, filed on May 29, 2009, now Pat. No. 8,980,300, which is a continuation of application No. 10/913,607, filed on Aug. 5, 2004, now abandoned.

(51) Int. Cl.
| | |
|---|---|
| *A61F 2/00* | (2006.01) |
| *A61K 39/00* | (2006.01) |
| *A61F 2/06* | (2013.01) |
| *A61F 2/02* | (2006.01) |
| *A61K 38/22* | (2006.01) |
| *A61K 38/00* | (2006.01) |
| *A61K 31/44* | (2006.01) |
| *A61K 31/445* | (2006.01) |
| *A61K 47/34* | (2006.01) |
| *A61L 27/34* | (2006.01) |
| *A61L 27/50* | (2006.01) |
| *A61L 31/10* | (2006.01) |
| *A61L 31/14* | (2006.01) |
| *A61K 31/436* | (2006.01) |
| *C08K 5/1575* | (2006.01) |
| *C09D 167/00* | (2006.01) |

(52) U.S. Cl.
CPC ............ *A61K 47/34* (2013.01); *A61K 31/436* (2013.01); *A61L 27/34* (2013.01); *A61L 27/502* (2013.01); *A61L 31/10* (2013.01); *A61L 31/141* (2013.01); *C08K 5/1575* (2013.01); *C09D 167/00* (2013.01)

(58) Field of Classification Search
None
See application file for complete search history.

(56) References Cited

U.S. PATENT DOCUMENTS

| | | |
|---|---|---|
| 2,158,107 A | 5/1939 | Gurruthers et al. |
| 2,260,295 A | 10/1941 | Gurruthers et al. |
| 2,350,388 A | 6/1944 | Claborn |
| 2,371,281 A | 3/1945 | Claborn |
| 2,917,410 A | 12/1959 | Vitalis |
| 4,273,137 A | 6/1981 | Pravoverov et al. |
| 4,539,981 A | 9/1985 | Tunc |
| 4,645,503 A | 2/1987 | Lin et al. |
| 4,655,771 A | 4/1987 | Wallsten |
| 4,979,822 A | 12/1990 | Sommer |
| 5,085,629 A | 2/1992 | Goldberg et al. |
| 5,304,121 A | 4/1994 | Sahatjian |
| 5,342,621 A | 8/1994 | Eury et al. |
| 5,433,751 A | 7/1995 | Christel et al. |
| 5,447,724 A | 9/1995 | Helmus et al. |
| 5,464,650 A | 11/1995 | Berg et al. |
| 5,468,253 A | 11/1995 | Bezwada et al. |
| 5,487,897 A | 1/1996 | Polson et al. |
| 5,496,359 A | 3/1996 | Davidson |
| 5,508,036 A | 4/1996 | Bakker et al. |
| 5,522,895 A | 6/1996 | Mikos |
| 5,539,081 A | 7/1996 | Gruber et al. |
| 5,581,387 A | 12/1996 | Cahill |
| 5,624,411 A * | 4/1997 | Tuch .............................. 604/265 |
| 5,637,113 A | 6/1997 | Tartaglia et al. |
| 5,649,977 A | 7/1997 | Campbell |

(Continued)

FOREIGN PATENT DOCUMENTS

| | | |
|---|---|---|
| EP | 0761712 | 3/1997 |
| EP | 0 950 386 | 10/1999 |

(Continued)

OTHER PUBLICATIONS

"Inherent Viscosity vs Molecular Weight," LACTEL Absorbable Polymers, http://absorbables.com/technical/inherent_viscosity.html, Nov. 4, 2013, pp. 1-3.
Cai et al. "Synthesis and Characterization of Polycaprolactone (B)-Poly(lactide-co-glycolide) (A) ABA Block Copolymer," Polym. Adv. Technol., 2000, vol. 11, pp. 159-166.
Filachione et al., "Lactic Acid Derivatives as Plasticizers Esters of Polymeric Lactic Acid," Bur. Agric. and Ind. Chem., 1951 pp. 1-19.
Handbook of Pharmaceutical Excipients, Am. Pharm. Assoc. pp. 209-213 (polyethylene glycol) (1986).

(Continued)

Primary Examiner — Jeffrey T Palenik
(74) Attorney, Agent, or Firm — Squire Patton Boggs (US) LLP

(57) ABSTRACT

A biocompatible plasticizer useful for forming a coating composition with a biocompatible polymer is provided. The coating composition may also include a biobeneficial polymer and/or a bioactive agent. The coating composition can form a coating on an implantable device. The implantable device can be used to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

21 Claims, No Drawings

(56) References Cited

U.S. PATENT DOCUMENTS

| | | | |
|---|---|---|---|
| 5,665,428 A | 9/1997 | Cha et al. | |
| 5,670,161 A | 9/1997 | Healy et al. | |
| 5,674,192 A | 10/1997 | Sahatjian et al. | |
| 5,674,286 A | 10/1997 | D'Alessio et al. | |
| 5,700,901 A | 12/1997 | Hurst et al. | |
| 5,702,717 A | 12/1997 | Cha et al. | |
| 5,741,329 A | 4/1998 | Agrawal et al. | |
| 5,747,637 A | 5/1998 | Shinoda et al. | |
| 5,824,048 A | 10/1998 | Tuch | |
| 5,824,049 A | 10/1998 | Ragheb et al. | |
| 5,824,059 A | 10/1998 | Wijay | |
| 5,834,582 A | 11/1998 | Sinclair et al. | |
| 5,955,096 A | 9/1999 | Santos et al. | |
| 5,980,564 A | 11/1999 | Stinson | |
| 6,077,989 A | 6/2000 | Kandel et al. | |
| 6,121,410 A | 9/2000 | Gruber et al. | |
| 6,143,863 A | 11/2000 | Gruber et al. | |
| 6,153,252 A * | 11/2000 | Hossainy et al. | 427/2.3 |
| 6,174,329 B1 | 1/2001 | Callol et al. | |
| 6,214,901 B1 | 4/2001 | Chudzik et al. | |
| 6,224,622 B1 | 5/2001 | Kotzev | |
| 6,235,061 B1 | 5/2001 | Laurencin et al. | |
| 6,240,616 B1 | 6/2001 | Yan | |
| 6,241,771 B1 | 6/2001 | Gresser et al. | |
| 6,251,136 B1 | 6/2001 | Guruqaiya et al. | |
| 6,335,029 B1 | 1/2002 | Kamath et al. | |
| 6,368,658 B1 | 4/2002 | Schwarz et al. | |
| 6,747,121 B2 | 6/2004 | Gogolewski et al. | |
| 6,780,424 B2 | 8/2004 | Claude | |
| 6,840,961 B2 | 1/2005 | Tofighi et al. | |
| 6,916,788 B2 | 7/2005 | Seo et al. | |
| 6,939,376 B2 | 9/2005 | Schulze et al. | |
| 7,018,401 B1 | 3/2006 | Hyodoh et al. | |
| 7,153,520 B2 | 12/2006 | Seo et al. | |
| 7,160,592 B2 | 1/2007 | Rypacek et al. | |
| 7,202,325 B2 | 4/2007 | Hossainy | |
| 7,244,443 B2 | 7/2007 | Pacetti | |
| 7,247,313 B2 | 7/2007 | Roorda et al. | |
| 7,255,891 B1 | 8/2007 | Pacetti | |
| 7,261,946 B2 | 8/2007 | Claude | |
| 7,288,609 B1 | 10/2007 | Pacetti | |
| 7,291,166 B2 | 11/2007 | Cheng et al. | |
| 7,294,329 B1 | 11/2007 | Ding | |
| 7,311,980 B1 | 12/2007 | Hossainy et al. | |
| 7,807,211 B2 | 10/2010 | Hossainy et al. | |
| 7,820,732 B2 | 10/2010 | Hossainy et al. | |
| 8,551,512 B2 | 10/2013 | Hossainy et al. | |
| 8,980,300 B2 * | 3/2015 | Pacetti et al. | 424/426 |
| 2001/0007083 A1 | 7/2001 | Roorda | |
| 2002/0016625 A1 | 2/2002 | Falotico et al. | |
| 2002/0041898 A1 | 4/2002 | Unger et al. | |
| 2002/0107330 A1 | 8/2002 | Pinchuk et al. | |
| 2003/0059454 A1 | 3/2003 | Barry et al. | |
| 2003/0069629 A1 | 4/2003 | Jadhav et al. | |
| 2003/0072868 A1 | 4/2003 | Harish et al. | |
| 2003/0073961 A1 | 4/2003 | Happ | |
| 2003/0082368 A1 | 5/2003 | Reuter et al. | |
| 2003/0083646 A1 | 5/2003 | Sirhan et al. | |
| 2003/0083740 A1 | 5/2003 | Pathak | |
| 2003/0139567 A1 | 7/2003 | Kim et al. | |
| 2003/0158517 A1 | 8/2003 | Kokish | |
| 2003/0190406 A1 | 10/2003 | Hossainy | |
| 2003/0199993 A1 | 10/2003 | Gellman et al. | |
| 2003/0216307 A1 | 11/2003 | Kohn et al. | |
| 2003/0236320 A1 | 12/2003 | Martin et al. | |
| 2004/0001872 A1 | 1/2004 | Shih et al. | |
| 2004/0009226 A1 | 1/2004 | McHugh et al. | |
| 2004/0052858 A1 | 3/2004 | Wu et al. | |
| 2004/0060508 A1 | 4/2004 | Pacetti | |
| 2004/0062853 A1 | 4/2004 | Pacetti et al. | |
| 2004/0106987 A1 | 6/2004 | Palasis et al. | |
| 2004/0138333 A1 | 7/2004 | Kim et al. | |
| 2004/0148002 A1 | 7/2004 | Cheng et al. | |
| 2004/0162609 A1 | 8/2004 | Hossainy et al. | |
| 2004/0180132 A1 | 9/2004 | Pacetti | |
| 2004/0191405 A1 | 9/2004 | Kerrigan | |
| 2004/0199241 A1 | 10/2004 | Gravett et al. | |
| 2004/0220656 A1 | 11/2004 | Epstein et al. | |
| 2004/0253203 A1 | 12/2004 | Hossainy et al. | |
| 2005/0021127 A1 | 1/2005 | Kawula | |
| 2005/0074544 A1 | 4/2005 | Pacetti et al. | |
| 2005/0112170 A1 | 5/2005 | Hossainy et al. | |
| 2005/0112172 A1 | 5/2005 | Pacetti | |
| 2005/0118344 A1 | 6/2005 | Pacetti | |
| 2005/0214339 A1 | 9/2005 | Tang et al. | |
| 2005/0226991 A1 | 10/2005 | Hossainy et al. | |
| 2005/0233062 A1 | 10/2005 | Hossainy et al. | |
| 2005/0265960 A1 | 12/2005 | Pacetti et al. | |
| 2005/0271700 A1 | 12/2005 | Desnoyer et al. | |
| 2005/0277577 A1 | 12/2005 | Hunter et al. | |
| 2005/0287184 A1 | 12/2005 | Hossainy et al. | |
| 2006/0002968 A1 | 1/2006 | Stewart et al. | |
| 2006/0034888 A1 | 2/2006 | Pacetti et al. | |
| 2006/0035854 A1 | 2/2006 | Goldstein et al. | |
| 2006/0041102 A1 | 2/2006 | Hossainy et al. | |
| 2006/0047095 A1 | 3/2006 | Pacetti et al. | |
| 2006/0062821 A1 | 3/2006 | Simhambhatla et al. | |
| 2006/0088571 A1 | 4/2006 | Chen et al. | |
| 2006/0089485 A1 | 4/2006 | DesNoyer et al. | |
| 2006/0093771 A1 | 5/2006 | Rypacek et al. | |
| 2006/0095122 A1 | 5/2006 | Pacetti | |
| 2006/0115449 A1 | 6/2006 | Pacetti | |
| 2006/0171985 A1 | 8/2006 | Richard et al. | |
| 2006/0246108 A1 | 11/2006 | Pacetti et al. | |
| 2007/0032853 A1 | 2/2007 | Hossainy et al. | |

FOREIGN PATENT DOCUMENTS

| | | |
|---|---|---|
| JP | 07163654 A2 | 6/1995 |
| JP | 09-511666 | 11/1997 |
| JP | 09-511741 | 11/1997 |
| JP | 2003-532489 | 11/2003 |
| WO | WO 95/27481 | 10/1995 |
| WO | WO 95/28124 | 10/1995 |
| WO | WO 01/85061 | 11/2001 |
| WO | WO 02/18477 | 3/2002 |
| WO | WO 03/082368 A1 | 10/2003 |
| WO | WO 2004/108111 | 12/2004 |
| WO | WO 2005/053571 | 6/2005 |
| WO | WO 01/45763 | 6/2011 |
| WO | WO 01/87368 A1 | 11/2011 |

OTHER PUBLICATIONS

International Preliminary Report mailed Jan. 5, 2010, for PCT Application No. PCT/US2008/064585, filed May 22, 2008, 6 pp.
Jain R., The manufacturing techniques of various drug loaded biodegradable poly(lactide-co-glycolide) (PLGA) devices (2000) Biomaterials 21:2475-2490.
Joziasse et al. "Rubber toughened linear and star-shaped poly(d,l-lactide-*co*-glycolide): synthesis, properties and in vitro degradation," Polymer, 1998, vol. 39, No. 2, pp. 467-474.
Kricheldorf, et al. "A-B-A-Triblock and mutiblock copolyesters prepared from $_\epsilon$-caprolactone, glycolide and $_L$-lactide by means of bismuth subsalicylate," Polymers 46, 2005, pp. 3248-3256.
Lactel, Absorbable Polymers Inherent Viscosity vs. Molecular Weight, downloaded from: www.absorbables.com/inherentviscosity.htm, Jun. 15, 2010, 2 pp.
Merriam-Webster Online Dictionary: "prodrug" (http://www.merriam-webster.com/medical/prodrug), 2010, pp. 1-2.
Windholz et al. Ed. The Merck Index "Lactic/Lactic Acid," Merck & Co., 1976, pp. 1-2.
Rodriguez, Ferdinanad, *Principles of Polymer Systems*, Fourth edition, Taylor&Francis, 1996, Title page and p. 1, 3 pages.
Fried, Joel R., *Polymer Science and Technology*, Prentice Hall, Englewood Cliffs, New Jersey, 1995, Title page and pp. 1, 2, and 4, 5, pages.
"Oligomer," http://www.yourdictionary.com/oligomer, Jul. 14, 2014, 2pp.
"Polymer," http://www.thefreedictionary.com/polymer, Jul. 14, 2014, pp. 1-3.

(56) References Cited

OTHER PUBLICATIONS

"Oligomer," http://www.thefreedictionary.com/oligomer, Jul. 14, 2014, pp. 1-2.
Scapin et al., "Use of triethylcitrate plasticizer in the production of poly-L-lactic acid implants with different degradation times," *J. Mater. Sci.: Mater. In Med.* 14:635-640 (2003).
Final Office Action in U.S. Appl. No. 10/913,607, mailed on Jan. 29, 2009; 11 pages.
Amendment in U.S. Appl. No. 10/913,607, filed Aug. 15, 2008; 15 pages.

* cited by examiner

PLASTICIZERS FOR COATING COMPOSITIONS

CROSS-REFERENCE TO RELATED APPLICATION

This application is a continuation of U.S. application Ser. No. 12/475,296, filed on May 29, 2009, published as US 2009-0238854 A1 on Sep. 24, 2009, and issuing as U.S. Pat. No. 8,980,300 B2 on Mar. 17, 2015, which is a continuation application of U.S. application Ser. No. 10/913,607, filed on Aug. 5, 2004, now abandoned; the teachings of both of which are incorporated herein in their entirety by reference.

BACKGROUND OF THE INVENTION

Field of the Invention

This invention generally relates to a plasticizer for coating compositions for coating an implantable device such as a drug-delivery stent.

Description of the Background

Degradable polymers have found numerous medical applications. One of these applications is to serve as a coating material for stents. However, articles formed of these biodegradable polymers may have undesirable properties, e.g., lack of flexibility, low elongation, too low a drug permeability, or poor processability. One of the commonly used methods to circumvent these shortcomings is to use a plasticizer.

Some most commonly used plasticizers are petrochemicals such as phthalates. Another commonly used plasticizer is epoxided vegetable oil. Some other materials such as small organic molecules, or inorganic materials, such as phosphoric acid can be used as plasticizers. However, many of these plasticizers either lack biocompatibility or have other undesirable properties. For example, petrochemical plasticizers such as phthalates are often toxic chemicals, and epoxided vegetable oil at higher levels may not mix properly into the plastics formulation or may cause plastics formulations to become brittle. Small organic molecules can also be toxic. In addition, they may have high vapor pressures, which may cause them to diffuse out of an article containing such a plasticizer and create shelflife stability issues because the mechanical integrity and the drug release rate, in the case of coating on a drug-delivery stent, will change over time.

Therefore, there is a need for plasticizers for use in coating compositions for coating a medical device such as a drug-delivery stent.

The compositions and the coatings formed thereof disclosed herein address the above described problems and needs.

SUMMARY OF THE INVENTION

Provided herein is a plasticizer that can be used with a biocompatible polymeric material to form a coating composition for coating an implantable device such as a stent. The plasticizer is biocompatible and non-volatile. The biocompatible polymeric material can be a biodegradable or non-biodegradable polymer. The coating composition can optionally include at least one bioactive agent.

The implantable device can be a stent that can be a metallic, biodegradable or nondegradable stent. The stent can be intended for neurovasculature, carotid, coronary, pulmonary, aorta, renal, biliary, iliac, femoral, popliteal, or other peripheral vasculature. The implantable device may be used to prevent or treat a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

DETAILED DESCRIPTION

Provided herein is a plasticizer that can be used with a biocompatible polymeric material to form a coating composition for coating an implantable device such a stent. In some embodiments, for example, stents made from a biodegradable material, the plasticizer can be included in the material from which the stent is made. The plasticizer is biocompatible and non-volatile. The biocompatible polymeric material can be a biodegradable or non-biodegradable polymer. The polymer can also be bioabsorbable or non-absorbable. The coating composition can optionally include at least one bioactive agent and/or biobeneficial material.

The implantable device can be a stent that can be a metallic, biodegradable or nondegradable stent. The stent can be intended for neurovasculature, carotid, coronary, pulmonary, aorta, renal, biliary, iliac, femoral, popliteal, or other peripheral vasculature. The stent can be used to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

Biocompatible, Non-Volatile Plasticizers

The plasticizer described herein can be any chemical compound capable altering the coating mechanical properties, such as by altering, e.g., lowering, the glass transition temperature of the polymer. By doing so, certain desirable mechanical properties such as flexibility and elongation are imparted to the coating. In general, the plasticizer has no vapor pressure so it cannot diffuse via a vapor phase into other phases or components in the final package of an implantable device on which the coating includes the plasticizer. Migration of the plasticizer by contact, through diffusion, can be controlled by using very impermeable, protective sheaths. The plasticizer is compatible with the polymeric material such as poly(D,L-lactide) and plasticizes the polymeric material. In addition, when used in a drug-delivery coating, the plasticizer does not substantially, or significantly, affect the drug stability. Altering the drug release kinetics is possible, if desired, particularly by selection of the type and quantity of plasticizing compound. The plasticizer can be made to change the degradation rate of the polymer if desirable.

In general, the plasticizer can exist in any percentage capable of plasticizing the coating composition. An exemplary range of the plasticizer is 0.1% to 40% by weight of the coating composition. Another representative range of the plasticizer range is 1% to 20% by weight of the coating composition.

The following describes several embodiments of the plasticizer described herein.

A. Low Molecular Weight Oligomers of Monomers Forming a Biodegradable Polymer

In one embodiment, the plasticizer can be low molecular weight oligomers of monomers forming a biodegradable polymer. For example, the oligomer can be a dimer, trimer, tetramers or oligomers of lactic acid, which forms PDLL or poly(D,L-lactic acid) (PDLLA). The low molecular weight oligomer can be a cyclic oligomer or a linear oligomer. In some embodiments, the plasticizer has the structure of formula I:

Formula I

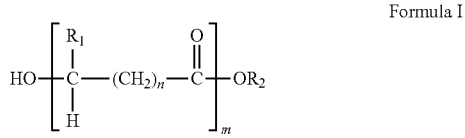

In some other embodiments, the plasticizer has the structure of formula II:

Formula II

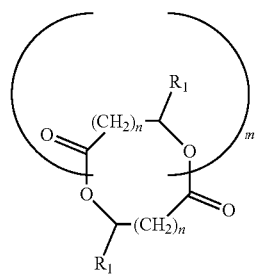

$R_1$, $R_2$, n and m of formula I and $R_1$, n and m of formula II are defined as follows:

$R_1$ and $R_2$ taken independently can be H, $CH_3$, and C2-C8 alkyl, alkyl, cycloalkyl, phenyl, halo, alkoxy, poly (ethylene glycol), carboxyl, alkylthiol, ketal, acetal, $C_2$-$C_8$ ketone containing group, benzyl, $C_2$-$C_8$ containing a protected amino group, or $C_2$-$C_8$ moiety containing unsaturation;

n can be 0 or a positive integer, for example, 1, 2, 3, 4, 5, 6, or 7; and m can be any positive integer, for example, an integer in the range between 1 to 100.

Preferred plasticizers will have molecular weights less than 10,000 daltons.

Some exemplary plasticizers of formulae I or II are cyclic or linear oligomers of glycolic acid, L-lactic acid, D-lactic acid, D,L-lactic acid, 3-hydroxypropanoic acid, 3-hydroxybutyric acid, 4-hydroxybutyric acid, 3-hydroxyvalerate, 4-hydroxyvalerate, 5-hydroxyvalerate, 3-hydroxyhexanoate, 4-hydroxyhexanoate, 5-hydroxyhexanoate, ε-caprolactone, 6-hydroxycaproic acid, γ-butyrolactone, β-butyrolactone and combinations thereof. Some other exemplary plasticizer of formula I can be dimer, trimer of lactic acid. In one embodiment, the plasticizer is an oligomer of poly(D,L-lactic acid) (PDLLA) having a molecular weight in the range from 1000 Daltons to 5,000 Daltons.

The low molecular weight oligomers described herein, for example plasticizers of formulae I or II, can be formed by methods documented in the art (see, for example, see, for example, Michael Smith, Organic Synthesis, 2$^{nd}$ Edition, McGraw-Hill, 2001). In one embodiment, the oligomer can be formed by controlled hydrolysis of a biodegradable polymer. For example, oligomers of 3-hydroxybutyric acid or polylactide can be formed by hydrolyzing poly(3-hydroxybutyric acid) (see, for example, Seebach, et al., Organic Syntheses, CV 9: 483; Tsuji and Nakahara, J. Appl. Polymer Science, 88(1):186-194 (2002)). Cyclic oligomers, for example cyclic oligomers of poly(ethylene terephthalate), can be formed by cyclization of short-chain linear oligomers, cyclodepolymerization from chain ends of a polymer, or ester-interchange reaction occurring randomly within or between polymer chains of a polymer (see, e.g., Cho, et al., Macromol. Chem. Phys. 202:998-1003 (2001)). Scheme 1 shows formation of a lactic acid trimer (Scheme I):

Scheme I

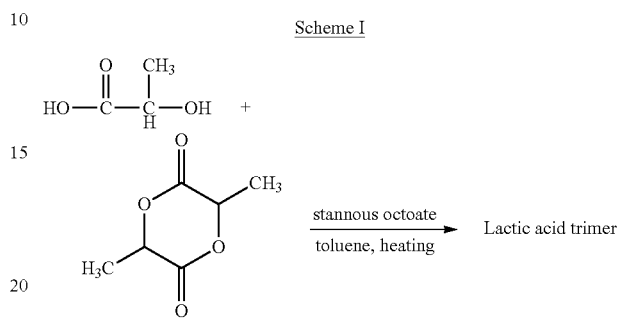

The plasticizer of formula I, produced by scheme I, has a terminal carboxy group. This may affect the stability of a drug in a drug-delivery coating that includes the plasticizer under in vivo conditions. For example, everolimus has a lactone functionality. The existence of a free acid end group in a plasticizer in a drug-delivery coating containing everolimus may cause the lactone group in everolimus to undergo the hydrolytic reaction. A free acid end group can be avoided by either using a different initiator in the plasticizer synthesis or by esterifying the acid endgroup. One example of using a different initiator in the ring opening synthesis, which yields an ester endgroup, is shown in Scheme II.

Scheme II

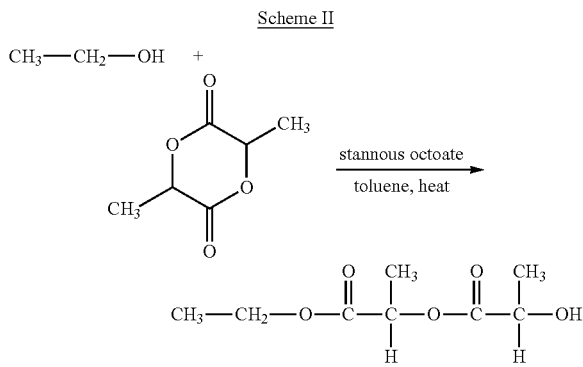

B. Fatty Acids

In another embodiment, the plasticizer can be a fatty acid. The fatty acid can be synthetic or naturally occurring fatty acids. Some fatty acids are endogenous compounds. The fatty acids may be saturated or unsaturated. The fatty acid can be liquid or solid, preferably liquid fatty acids. Representative natural fatty acids include, but are not limited to, palmitoleic acid, lauric acid, oleic acid, linoleic acid, and arachidonic acid. Representative synthetic fatty acids include, for example, C6-C15 alkanoic acids such as hexanoic acid, heptanoic acid, or octanoic acid.

C. Fatty Acid Esters

In a further embodiment of the present invention, the plasticizer described herein can be esters of the fatty acids. The ester can be made to be miscible with the polymer forming the coating on an implantable device by selecting a hydrocarbon chain, e.g., an alkyl chain, to form the ester group. The term "miscible" as used herein means the ester has a substantial solubility in the polymer. Fatty acid esters would not influence the polymer degradation kinetics of the coating polymer or stability of the drug in a drug-delivery coating. For example, useful plasticizers can be the ethyl, propyl, or butyl ester of oleic acid, which are all commercially available.

D. Glycerides

In a further embodiment, the plasticizers can be a glyceride. The glyceride can be a mono, di, or triglyceride. Triglycerides are already present in the blood stream. The glycerides can be natural glycerides or synthetic glycerides and can contain any of the fatty acids described above. For example, most naturally occurring triglycerides contain stearate, palmitate, linoleic, oleic fatty acid, or a mixture thereof.

E. Fatty Alcohols

In still a further embodiment, the plasticizer can be a fatty alcohol. The fatty alcohol can be synthetic or naturally occurring fatty alcohols. Some representative fatty alcohols include, but are not limited to, fatty alcohols described in the FDA GRAS (generally recognized as safe) list.

E. Other Plasticizers

The plasticizer described herein can be any other materials that are biocompatible and compatible with the coating polymer. For example, citric acid esters have been studied as plasticizers for poly(L-lactide) (Scapin, S M N, et al., J. Mater. Sci.: Mater. In Med. 14:635-640 (2003)). Some other plasticizers that may be useful include, for example, the plasticizers described in U.S. Pat. Nos. 4,399,248; 4,426,542; 4,938,971; 5,189,105; 4,857,573; 5,248,531; and 5,688,850.

In some embodiments, the plasticizer described herein can be, for example, L-lactic acid, D-lactic acid or D,L-lactic acid monomer, a lactic acid derivative such as ethyl lactate, a polyalkylene glycol such as polyethylene glycol (PEG) or a polyalkylene oxide or combinations thereof. Ethyl lactide has a relatively low boiling point of 154° C. It can move via vapor in the package on storage, but a lactide of a higher alkyl group such as propyl lactide or butyl lactide have a higher boiling point. PEG is very hydrophilic and will tend to increase the drug release rate by increased water swelling, but this can be offset by lowering the drug/polymer ratio. In some other embodiments, the plasticizer can also be one of biocompatible esters, glycolic acid, 3-hydroxypropanoic acid, 3-hydroxybutyric acid, 4-hydroxybutyric acid, 3-hydroxyvalerate, 4-hydroxyvalerate, 5-hydroxyvalerate, 3-hydroxyhexanoate, 4-hydroxyhexanoate, 5-hydroxyhexanoate, ε-caprolactone, 6-hydroxycaproic acid, γ-butyrolactone, β-butyrolactone or combinations thereof.

Another class of useful plasticizers can be a bioactive molecule or an oligomer thereof capable of plasticizing a coating composition. One of such plasticizers can be aspirin, oligomeric aspirin, the bioactive agents defined below, e.g., everolimus, or pimecrolimus.

A further class of plasticizers can be a low molecular weight polymer having a molecular weight, e.g., below 10,000 Daltons. In some embodiments, the plasticizer can be a hydrophilic material, derivatized hydrophilic material, hydrophobic material, or derivatized hydrophobic material. In some embodiments, the hydrophilic material can be a hydrophilic polymer such as poly(ethylene glycol) (PEG), polyvinylpyrrolidone (PVP), poly(vinyl alcohol) (PVA), polyacrylamide (PAAm), mannose-6-phosphate, quaternary silanes, or combinations thereof. The hydrophobic material can be the biocompatible polymer described below with low molecular weight, some examples of which are low molecular weight poly(ester amide), low molecular weight polyglycerol sebacic acid, and low molecular with triblock poly(D,L-lactic acid)-co-poly(ethylene glycol)-co-poly(D, L-lactic acid) (PDLLA-PEG-PDLLA). Low molecular weight generally means a molecular weight below, e.g., 10,000 Daltons. The low molecular hydrophobic polymer can be modified or derivatized using, e.g., a bioactive agent defined below, one of which is RGD. An exemplary modified or derivatized low molecular weight hydrophobic material is RGD modified poly(D,L-lactic acid).

Biocompatible Polymer

The biocompatible polymer useful for forming a coating composition with the plasticizers described herein can be any biocompatible polymer known in the art, which can be biodegradable or nondegradable. Biodegradable is intended to include bioabsorbable or bioerodable. Representative examples of polymers that can be used to coat an implantable device in accordance with the present invention include, but are not limited to, poly(ester amide), ethylene vinyl alcohol copolymer (commonly known by the generic name EVOH or by the trade name EVAL), poly(L-lactide), poly(D-lactide), poly(D,L-lactide), poly(D,L-lactide-co-L-lactide), poly(L-lactide-co-glycolide), poly(D,L-lactide-co-glycolide) (PDLLAGA), poly(L-lactide-co-caprolactone), poly(D,L-lactide-co-caprolactone), poly(hydroxyvalerate), polycaprolactone, poly(hydroxybutyrate), poly(hydroxybutyrate-co-valerate), polydioxanone, polyorthoester, polyanhydride, poly(glycolic acid), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether; polyvinylidene halides, fluoro polymers or copolymers under the trade name Solef™ or Kynar™ such as polyvinylidene fluoride (PVDF) and poly (vinylidene fluoride-co-hexafluoropropylene), polyvinylidene chloride, poly(butyl methacrylate), polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, polyvinylpyrrolidone (PVP), poly(vinyl alcohol) (PVA), polyacrylamide (PAAm), poly(glyceryl sebacate), poly(propylene fumarate), epoxy resins, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose.

The biocompatible polymer can provide a controlled release of a bioactive agent, if included in the coating and/or binding the bioactive agent to a substrate, which can be the surface of an implantable device or a coating thereon. Controlled release and delivery of bioactive agent using a polymeric carrier has been extensively researched in the past several decades (see, for example, Mathiowitz, Ed., Encyclopedia of Controlled Drug Delivery, C.H.I.P.S., 1999). For example, PLA based drug delivery systems have provided controlled release of many therapeutic drugs with various degrees of success (see, for example, U.S. Pat. No. 5,581, 387 to Labrie, et al.). The release rate of the bioactive agent can be controlled by, for example, by selection of a particular type of biocompatible polymer which can provide a desired release profile of the bioactive agent. The release profile of the bioactive agent can be further controlled by the molecular weight of the biocompatible polymer and/or the ratio of the biocompatible polymer over the bioactive agent. In the case of a biodegradable polymer, the release profile can also be controlled by the degradation rate of the biodegradable polymer. One of ordinary skill in the art can readily select a carrier system using a biocompatible polymer to provide a controlled release of the bioactive agent.

A preferred biocompatible polymer is a polyester, such as one of poly(ester amide), poly(D,L-lactide) (PDLLA), poly (D,L-lactic acid-co-glycolic acid) (PDLLGA), polyglycolic acid (PGA), polyhydroxyalkanoate (PHA), poly(3-hydroxybutyrate) (PHB), poly(3-hydroxybutyrate-co-3-hydroxyvalerate), poly((3-hydroxyvalerate), poly(3-hydroxyhexanoate), poly(4-hydroxybutyrate), poly(4-hydroxyvalerate), poly(4-hydroxyhexanoate), poly(D,L-lactide), poly(L-lactide), polycaprolactone (PCL) and a combination thereof.

Biobeneficial Material

The coating containing the plasticizer described herein may further include a biobeneficial material. The biobeneficial material can be a polymeric material or non-polymeric material. The biobeneficial material is preferably flexible when present as a discrete layer, or confers elastic properties in a blend or copolymer, and is biocompatible and/or biodegradable, more preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent. As used herein, the term non-fouling is defined as preventing, delaying or reducing the amount of formation of protein build-up caused by the body's reaction to foreign material and can be used interchangeably with the term "anti-fouling."

Representative biobeneficial materials include, but are not limited to, polyethers such as poly(ethylene glycol), copoly (ether-esters) (e.g. PEO/PLA); polyalkylene oxides such as poly(ethylene oxide), polypropylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropyl methacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), polystyrene-polyisoprene-polystyrene-co-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, and combinations thereof. In some embodiments, the polymer can exclude any one of the aforementioned polymers.

In a preferred embodiment, the biobeneficial material is a block copolymer comprising flexible poly(ethylene glycol) terephthalate)/poly(butylenes terephthalate) (PEGT/PBT) segments (PolyActive™). These segments are biocompatible, non-toxic, non-antigenic and non-immunogenic. Previous studies have shown that the PolyActive™ top coat decreases the thrombosis and embolism formation on stents. PolyActive™ is generally expressed in the form of xPEG-TyPBTz, in which x is the molecular weight of PEG, y is percentage of PEGT, and z is the percentage of PBT. A specific PolyActive™ polymer can have various ratios of the PEG, ranging from about 1% to about 99%, e.g., about 10% to about 90%, about 20% to about 80%, about 30% to about 70%, about 40% to about 60% PEG. The PEG for forming PolyActive™ can have a molecular weight ranging from about 300 Daltons to about 100,000 Daltons, e.g., about 300 Daltons, about 500 Daltons, about 1,000 Daltons, about 5,000 Daltons, about 10,000 Daltons, about 20,000 Daltons, or about 50,000 Daltons.

In another preferred embodiment, the biobeneficial material can be a polyether such as polyethylene glycol (PEG) or polyalkylene oxide.

Bioactive Agents

The plasticizers described herein can be used to form a coating on an implantable device with a polymeric material and optionally with one or more bioactive agents. Examples of such agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Other examples of drugs include antibodies, receptor ligands, and enzymes, adhesion peptides, oligosaccharides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Such agents can also include a prohealing drug that imparts a benign neointimal response characterized by controlled proliferation of smooth muscle cells and controlled deposition of extracellular matrix with complete luminal coverage by phenotypically functional (similar to uninjured, healthy intima) and morphologically normal (similar to uninjured, healthy intima) endothelial cells. Such agents can also fall under the genus of antineoplastic, cytostatic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include heparinoids, hirudin, recombinant hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, antibody, and thrombin inhibitors such as ANGIOMAX™ (bivalirudin, Biogen, Inc., Cambridge, Mass.). Examples of cytostatic agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.), actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Other drugs include calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium.

Other therapeutic substances or agents which may be appropriate include alpha-interferon, genetically engineered epithelial cells, bioactive RGD, antibodies such as CD-34 antibody, abciximab (REOPRO), and progenitor cell capturing antibody, prohealing drugs that promotes controlled proliferation of muscle cells with a normal and physiologically benign composition and synthesis products, enzymes, antivirals, anticancer drugs, anticoagulant agents, free radical scavengers, steroidal anti-inflammatory agents, non-steroidal anti-inflammatory agents, antibiotics, nitric oxide donors, super oxide dismutases, super oxide dismutases mimics, 4-amino-2,2,6,6-tetramethylpiperidine-1-oxyl (4-amino-TEMPO), dexamethasone, clobetasol, aspirin, estradiol, tacrolimus, rapamycin, rapamycin derivatives, 40-O-(2-hydroxy)ethyl-rapamycin (everolimus), pimecrolimus, 40-O-(3-hydroxy)propyl-rapamycin, 40-O-[2-(2-hydroxy)ethoxy]ethyl-rapamycin, 40-O-tetrazole-rapamycin, ABT-578, progenitor cell capturing antibody, pro-drugs thereof, co-drugs thereof, and a combination thereof. The foregoing substances are listed by way of example and are not meant to be limiting. Other active agents which are currently available or that may be developed in the future are equally applicable.

The dosage or concentration of the bioactive agent required to inhibit or promote a favorable therapeutic effect should be less than the level at which the bioactive agent produces toxic effects and greater than the level at which non-therapeutic results are obtained. The dosage or concentration of the bioactive agent required to inhibit the desired cellular activity of the vascular region can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. The bioactive compound can be incorporated into polymeric coating in a percent loading of between 0.01% and 70% by weight, more preferably between 5% and 50% by weight. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structures of the device for the treatment of patent foramen ovale, aneurysm coils, and embolic protection devices can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. For example, the plasticizer could be added to alter the body of a stent made from a biodegradable or bioabsorbable polymer.

Method of Use

In accordance with embodiments of the invention, a coating of the various described embodiments can be formed on an implantable device or prosthesis, e.g., a stent. For coatings including one or more active agents, the agent will remain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth examples. All parameters and data are not to be construed to unduly limit the scope of the embodiments of the invention.

Example 1

Prophetic Synthesis of an Oligomeric Dimer of D,L-Lactide

In this example, a conventional ring opening polymerization of D,L-lactide is performed using stannous octoate as a catalyst, and 1-hexanol as an initiator. A 2-necked, 100 ml flask equipped with stopcock, septum and stirbar can be flame dried under vacuum, and purged with argon. Inside an argon filled glove box, D,L-lactide (50 gm, 0.347 mol) is placed with stannous octoate (1.41 gm, 0.0347 mol). The reaction mixture can be heated in an oil bath with stirring to 140° C. At time zero, 1-hexanol is added (35.4 gm, 0.347 mol) and the reaction allowed to proceed for 2 hours. The reaction mixture is poured into 500 ml of methanol, the precipitated oil isolated, and dried under vacuum.

Example 2

Making a Stent Coating Using the Plasticizer of Example 1

A first composition can be prepared by mixing the following components:
(a) about 2.0 mass % of poly(D,L-lactide), and
(b) the balance, a 50/50 (w/w) blend of chloroform and 1,1,2-trichloroethane.

The first composition can be applied onto the surface of bare 12 mm small VISION stent (available from Guidant Corporation). The coating can be sprayed and dried to form a primer layer. A spray coater can be used having a 0.014 round nozzle maintained at ambient temperature with a feed pressure 2.5 psi (0.17 atm) and an atomization pressure of about 15 psi (1.02 atm). About 20 µg of the coating can be applied at per one spray pass. Between the spray passes the stent can be dried for about 10 seconds in a flowing air stream at about 50° C. About 100 µg of wet coating can be applied. The stents can be baked at about 80° C. for about one hour, yielding a primer layer composed of approximately 80 µg of poly(D,L-lactide).

A second composition is prepared by mixing the following components:
(a) 0.3 mass % of the plasticizer of Example 1,
(b) 1.8 mass % of poly(D,L-lactide),
(c) 0.9 mass % of everolimus, and
(d) the balance, a 50/50 blend by weight of chloroform and 1,1,2-trichloroethane.

The composition is applied onto the surface of the stent. Coating is sprayed and dried to form a drug reservoir layer. A spray coater is used having a 0.014 round nozzle maintained at ambient temperature with a feed pressure 2.5 psi (0.17 atm) and an atomization pressure of about 15 psi (1.02 atm). Coating is applied at 20 µg per pass, in between which the stent is dried for 10 seconds in a flowing air stream at 50° C. Approximately 500 µg of wet coating is applied. The stents are baked at 60° C. for one hour, yielding a drug reservoir layer composed of approximately 450 µg of coating.

Example 3

Making a Stent Coating Using a Cyclic Lactide as a Plasticizer

A layer of Parylene™ C, 5 microns thick, is applied to all surfaces of a bare 12 mm small VISION stent (available from Guidant Corporation), by thermal vapor deposition.

A composition is prepared by mixing the following components:
(a) 0.2 mass % of D,L-lactide monomer,
(b) 2.0 mass % of poly(D,L-lactide),
(c) 2.0 mass % of everolimus, and
(d) the balance, a 50/50 blend of acetone and 2-butanone.

The composition is applied onto only the abluminal surfaces of the VISION stent. Coating is applied using an inkjet microdispenser with CNC controller and imaging system to position the stent under the dispensing nozzle. Six passes are applied with 5 minutes of air drying between each pass. Approximately 300 µg of wet coating is applied. The stents are baked at 60° C. for one hour, yielding a drug reservoir layer composed of approximately 270 µg of coating.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A polymeric coating for an implantable device, the coating comprising a biocompatible polymer and a biocompatible plasticizer, the plasticizer being in the range between 0.1% and 40% by weight of the coating;
   wherein the plasticizer is a linear oligomer of a monomer selected from the group consisting of glycolic acid, L-lactic acid, D-lactic acid, D, L-lactic acid, 3-hydroxypropanoic acid, 3-hydroxybutyric acid, 4-hydroxybutyric acid, 3-hydroxyvalerate, 4-hydroxyvalerate, 5-hydroxyvalerate, 3-hydroxyhexanoate, 4-hydroxyhexanoate, 5-hydroxyhexanoate, ε-caprolactone, 6-hydroxycaproic acid, γ-butyrolactone, β-butyrolactone and combinations thereof;
   and
   wherein the linear oligomer is a dimer, a trimer, a tetramer, or a combination thereof.

2. The polymeric coating of claim 1, wherein the biocompatible polymer is bioabsorbable, biodegradable or nonabsorbable.

3. The polymeric coating of claim 1, wherein the biocompatible polymer is selected from the group consisting of poly(L-lactide), poly(D-lactide), poly(D,L-lactide), poly(D, L-lactide-co-L-lactide), poly(D,L-lactide-co-glycolide) (PDLLAGA), poly(L-lactide-co-glycolide), poly(L-lactide-co-caprolactone), poly(D,L-lactide-co-caprolactone), polyhydroxyalkanoates (PHA), poly(3-hydroxybutyrate) (PHB), poly(3-hydroxyhexanoate), poly(4-hydroxybutyrate), poly (3-hydroxyvalerate), poly(3-hydroxybutyrate-co-3-hydroxyvalerate), ethylene vinyl alcohol copolymer (EVOH), poly(glycolic acid-co-trimethylene carbonate), polyvinylidene chloride, polyacrylonitrile, Nylon 66, polycaprolactam, polyvinylpyrrolidone (PVP), poly(vinyl alcohol) (PVA), polyacrylamide (PAAm), poly(glyceryl sebacate), poly(propylene fumarate), rayon, rayon-triacetate, cellulose acetate, cellulose butyrate, cellulose acetate butyrate, cellophane, cellulose nitrate, cellulose propionate, carboxymethyl cellulose, and combinations thereof.

4. The polymeric coating of claim 1, further comprising a biobeneficial material.

5. The polymeric coating of claim 4, wherein the biobeneficial material is selected from the group consisting of block copolymers of poly(ethylene glycol terephthalate)/poly(butylene terephthalate) (PEGT/PBT), poly(ethylene oxide-co-D,L-lactic acid) (PEO/PDLLA), poly(ethylene oxide), poly(propylene oxide), phosphoryl choline, choline, poly(aspirin), SIS-PEG, polystyrene-polyethylene glycol (polystyrene-PEG), polyisobutylene-PEG, PCL-PEG, PLA-PEG, poly(methyl methacrylate)-PEG (PMMA-PEG), poly(dimethyl-siloxane)-PEG (PDMS-PEG), poloxamer surfactants, poly(tetramethylene glycol), hydroxy functional poly(vinyl pyrrolidone), fibrin, fibrinogen, cellulose, starch, collagen, dextran, dextrin, hyaluronic acid, fragments of hyaluronic acid, heparin, fragments of heparin, glycosaminoglycans (GAG), polysaccharides, elastin, chitosan, alginate, and combinations thereof.

6. The polymeric coating of claim 1, further comprising a bioactive agent.

7. The polymeric coating of claim 6, wherein the bioactive agent is selected from the group consisting of steroids, anticancer agents, nucleic acids, peptides, proteins, antibodies, antibiotics, anesthetics, vaccines, anti-inflammatory drugs, anti-coagulant agents, antisense oligonucleotides, and combinations thereof.

8. The polymeric coating of claim 6, wherein the bioactive agent is selected from the group consisting of paclitaxel, docetaxel, estradiol, nitric oxide donors, super oxide dismutases, 4-amino-2,2,6,6-tetramethylpiperidine-1-oxyl (4-amino-TEMPO), tacrolimus, dexamethasone, rapamycin, 40-O-(2-hydroxy)ethyl-rapamycin (everolimus), pimecrolimus, 40-O-(3-hydroxy)propyl-rapamycin, 40-O-[2-(2-hydroxy)ethoxy]ethyl-rapamycin, 40-O-tetrazole-rapamycin, zotarolimus, clobetasol, bioactive RGD, CD-34 antibody, abciximab, progenitor cell capturing antibody, and combinations thereof.

9. The polymeric coating of claim 1, further comprising an oligomer of poly(D,L-lactic acid) (PDLLA) of a molecular weight in the range from 1000 Daltons to 5,000 Daltons.

10. The polymeric coating of claim 1, wherein the biocompatible polymer is selected from the group consisting of poly(ester amide)s, poly(hydroxyvalerate), polycaprolactone, polydioxanone, polyorthoesters, polyanhydrides, polyphosphoesters, polyphosphoester urethanes, poly(amino acids), polycyanoacrylates, poly(trimethylene carbonate), poly(iminocarbonates), polyurethanes, polyphosphazenes, polyesters, polyolefins, polyisobutylene and ethylene-alphaolefin copolymers, acrylic polymers and copolymers, vinyl halide polymers and copolymers, polyvinyl chloride, polyvinyl ethers, polyvinyl methyl ether, polyvinylidene halides, polyvinyl ketones, polyvinyl aromatics, polyvinyl esters, copolymers of vinyl monomers with each other and olefins, ethylene-methyl methacrylate copolymers, acrylonitrile-styrene copolymers, ABS resins, ethylene-vinyl acetate copolymers, polyamides, alkyd resins, polycarbonates, polyoxymethylenes, polyimides, polyethers, epoxy resins, polyurethanes, cellulose ethers, and combinations thereof.

11. The polymeric coating of claim 4, wherein the biobeneficial material is selected from the group consisting of poly(ether ester)s, polyalkylene oxalates, polyalkylene oxides, polyphosphazenes, polymers and co-polymers of hydroxyl bearing monomers, hydroxyethyl methacrylate (HEMA), hydroxypropyl methacrylate (HPMA), hydroxypropyl methacrylamide, alkoxymethacrylates, alkoxyacrylates, PEG acrylates (PEGA), PEG methacrylates, 2-methacryloyloxyethyl-phosphorylcholine (MPC) and n-vinyl pyrrolidone (VP), polymers and co-polymers of carboxylic acid bearing monomers, methacrylic acid (MA), acrylic acid (AA), and 3-trimethylsilylpropyl methacrylate (TMSPMA), biomolecules, silicones, and combinations thereof.

12. The polymeric coating of claim 4, wherein the biobeneficial material is selected from the group consisting of block copolymers of poly(ethylene glycol terephthalate)/poly(butylene terephthalate) (PEGT/PBT), poly(ether ester)s, polyalkylene oxalates, poly(ethylene oxide-co-D,L-lactic acid) (PEO/PDLLA), polyalkylene oxides, poly(ethylene oxide), poly(propylene oxide), polyphosphazenes, phosphoryl choline, choline, poly(aspirin), polymers and co-polymers of hydroxyl bearing monomers, hydroxyethyl methacrylate (HEMA), hydroxypropyl methacrylate (HPMA), hydroxypropyl methacrylamide, alkoxymethacrylate, alkoxyacrylate, PEG acrylate (PEGA), PEG methacrylate, 2-methacryloyloxyethylphosphorylcholine (MPC) and n-vinyl pyrrolidone (VP), polymers and co-polymers of carboxylic acid bearing monomers, methacrylic acid (MA), acrylic acid (AA), and 3-trimethylsilylpropyl methacrylate (TMSPMA), SIS-PEG, polystyrene-PEG, polyisobutylene-PEG, PCL-PEG, PLA-PEG, poly(methyl methacrylate)-PEG (PMMA-PEG), poly(dimethylsiloxane)-PEG (PDMS-PEG), PVDF-PEG, polypropylene oxide-co-polyethylene glycol surfactants, poly(tetramethylene glycol), hydroxy functional poly(vinyl pyrrolidone), fibrin, fibrinogen, cellulose, starch, collagen, dextran, dextrin, hyaluronic acid, fragments of hyaluronic acid, heparin, fragments of heparin, glycosamino glycan (GAG), polysaccharide, elastin, chitosan, alginate, silicones, and combinations thereof.

13. A method of treating a human being in need of treatment of a disorder comprising implanting in the human being a medical device comprising the polymeric coating of claim 1, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

14. A method of treating a human being in need of treatment of a disorder comprising implanting in the human being a medical device comprising the polymeric coating of claim 6, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

15. A method of treating a human being in need of treatment of a disorder comprising implanting in the human being a medical device comprising the polymeric coating of claim 7, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

16. A method of treating a human being in need of treatment of a disorder comprising implanting in the human being a medical device comprising the polymeric coating of claim 8, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

17. An implantable device comprising the polymeric coating of claim 1.

18. An implantable device comprising the polymeric coating of claim 6.

19. An implantable device comprising the polymeric coating of claim 7.

20. An implantable device comprising the polymeric coating of claim 8.

21. The polymeric coating of claim 1, wherein the plasticizer is in the range of 1% to 20% by weight of the coating.

* * * * *